US00PP09297P

United States Patent [19]

Lemon

[11] Patent Number: Plant 9,297

[45] Date of Patent: Sep. 19, 1995

[54] FLORIBUNDA GERANIUM 'JULIA'

[76] Inventor: David Lemon, 4176 Vanguard Dr., Lompoc, Calif. 93436

[21] Appl. No.: 281,736

[22] Filed: Jul. 27, 1994

[51] Int. Cl.[6] ..... A01H 5/00

[52] U.S. Cl. ..... Plt./87.12

[58] Field of Search ..... Plt. 87.12

*Primary Examiner*—James R. Feyrer

[57] ABSTRACT

The cultivar is characterized by its bright salmon color. Its compact, controlled growth habit and prolific blooms provide for superb cuttings and performs equally well in hanging baskets or in a ground bed. The blooms are heat tolerant.

1 Drawing Sheet

BACKGROUND OF THE NEW PLANT

The present invention comprises a new and distinct cultivar of *Pelargonium*×*hortorum* known by the varietal name Julia (Oglevee No. 9052, Bodger No. 9GM 82-1). The new variety was discovered in a selective breeding program by David Lemon at Bodger Seeds, Ltd., Lompoc, Calif. The new variety is a selection from the crossing of Aurora×Pink Floral Cascade.

The new cultivar was first asexually reproduced by cuttings at Ogleveed Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville Pa., using full light, 60° fahrenheit night temperature, 68° fahrenheit day temperature, 72° fahrenheit vent temperature and grown in a soilless media of constant fertilizer 200 to 250 part per million of nitrogen and potassium has a response time of six weeks from the rooted cutting to a flowering plant in a 10.0 cm pot.

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Feb. 9, 1993 and flowered Mar. 23, 1993 under full light and greenhouse, and colorings were taken indoors under 200–220 foot candles of fluorescent cool white light using the R.H.S. Colour Chart of The Royal Horticultural Society of London.

THE PLANT

Classification:

*Botanical.*—*Pelargonium*×*hortorum.*

Form: Semi-dwarf, compact, free basal branching; neat formal plant habit.

*Height.*—16.0–19.0 cm from the media surface.

*Growth.*—Lateral and cascading growth; free basal branching.

*Strength.*—Free standing; free and early flowering; multipurpose uses.

Foliage: Light zone present, stalked leaf attachment.

Leaves:

*Size.*—6.5–8.0 cm across.

*Shape.*—Reinform; cordate base.

*Margin.*—Crenate.

*Texture.*—Pubescent.

*Color.*—Top: Yellow/green Group 146A; Zone: Yellow/green Group 147A; Bottom: Yellow/-green Group 147B.

*Ribs and veins.*—Palmate venation: Color: Yellow/Green group 147C.

Petioles:

*Length.*—5.5–7.0 cm.

*Color.*—Yellow/green group 146C.

Stem:

*Color.*—Yellow/green group 146D.

*Internodes.*—2.0–3.5 cm in length.

THE BUD

Shape: Upright; hemispherical cluster.

Size: 2.0–3.0 cm across.

INFLORESCENCE

Blooming habit: Upright, continuous, very floriferous.

Size: 8.5–10.0 cm across.

Borne: floret on pedicel; pedicel on peduncle; 5.0–9.0 cm above foliage.

Florets:

*Form.*—Slightly cupped.

*Color.*—Top: Red group 38A; Bottom group 38B.

*Petals.*—9–12 in number; separate, not united; margin entire; obovate.

*Size.*—3.5–4.0 cm across.

*Texture and appearance.*—Smooth and satiny. Appearance from a distance is clean bright salmon flowers above medium green foliage.

Petaloids:

*Quantity.*—1 to 5.

*Shape.*—Narrow, twisted.

*Color.*—Red group 38A.

Pedicel:

*Length.*—2.0—2.5 cm.

*Color.*—Yellow/green group 146D.

Peduncle: Arises from node opposite leaf petiole.

*Length.*—10.0–16.6 cm in length.

*Color.*—Yellow/green group 146D.

Persistence:

*Disease resistance.*—Not known.

*Lasting Quality.*—Continuous blooming, heat tolerant.

REPRODUCTIVE ORGANS

Stamens:

*Anthers.*—2.0–3.0 mm in length.

*Filaments.*—5.0–7.0 mm in length; white with some pink lips.

*Pollen.*—Golden Brown.

Pistils:

*Number.*—One.

*Length.*—5.0–7.0 mm.

*Stigma.*—One; 5–6 parted, pink in color.

*Style.*—2.0–3.0 mm, pink in color.

Ovaries: Superior, pubescent; pale green in color, 4.0–5.0 mm in length, 2.0 mm across.

Fruit: Occasional fruit noted.

GENERAL CHARACTERISTICS

This new geranium variety, Julia, is an improvement on the current floribunda variety Judy. The flower form is improved with less petaloids and the flower color is a brighter salmon than Judy. The plant form is slightly larger yet very controlled in a neat mound habit.

For production purposes, Julia is a very good cutting producer and is very easy to root. Julia can be used in either hanging baskets or ground beds and will be a very prolific bloomer.

I claim:

1. A new and distinct variety of geranium plant, substantially as shown and described.

* * * * *

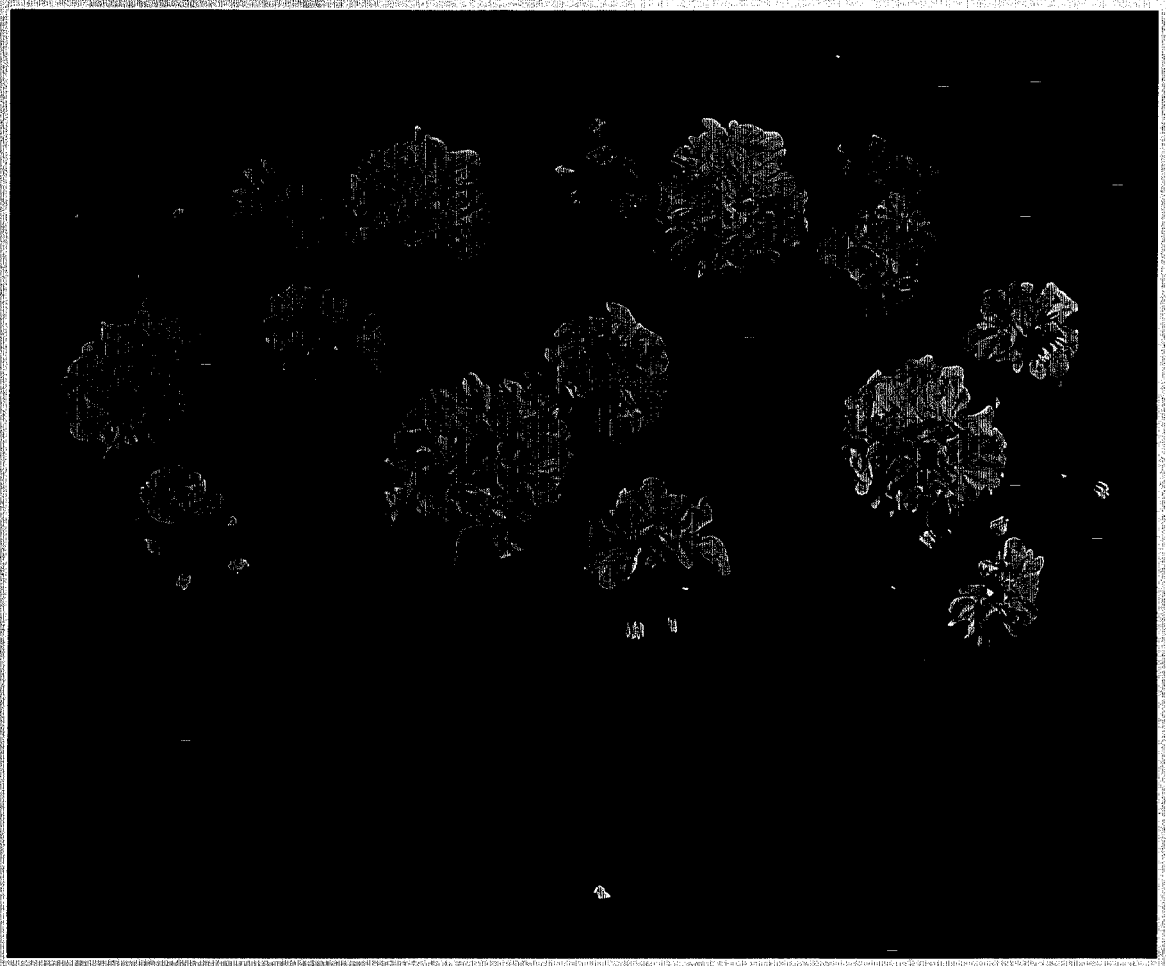

UNITED STATES PATENT AND TRADEMARK OFFICE

CERTIFICATE OF CORRECTION

PATENT NO. : Plant 9,297

DATED : September 19, 1995

INVENTOR(S) : David Lemon

It is certified that error appears in the above-identified patent and that said Letters Patent is hereby corrected as shown below:

Column 1, line 10, delete "Ogleveed" and insert in its place --Oglevee--.

Column 2, line 32, delete "Bottom group" and insert in its place --Bottom: Red group--.

Signed and Sealed this

Twenty-seventh Day of February, 1996

*Attest:*

*Attesting Officer*

BRUCE LEHMAN

*Commissioner of Patents and Trademarks*